United States Patent
Saito et al.

(10) Patent No.: US 10,517,554 B1
(45) Date of Patent: Dec. 31, 2019

(54) X-RAY FLUOROSCOPIC IMAGING APPARATUS

(71) Applicant: Shimadzu Corporation, Kyoto (JP)

(72) Inventors: Atsuo Saito, Kyoto (JP); Dai Hirose, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 0 days.

(21) Appl. No.: 16/124,265

(22) Filed: Sep. 7, 2018

(51) Int. Cl.
  *H05G 1/08* (2006.01)
  *A61B 6/00* (2006.01)
  *A61B 6/04* (2006.01)

(52) U.S. Cl.
  CPC .......... *A61B 6/4441* (2013.01); *A61B 6/0457* (2013.01); *A61B 6/467* (2013.01); *A61B 6/547* (2013.01)

(58) Field of Classification Search
  CPC ..... A61B 6/4441; A61B 6/0457; A61B 6/467; A61B 6/547
  See application file for complete search history.

(56) References Cited

U.S. PATENT DOCUMENTS

| | | | |
|---|---|---|---|
| 5,930,328 A | 7/1999 | Nakamura et al. | |
| 6,416,219 B1 | 7/2002 | Pflaum et al. | |
| 7,000,271 B2 | 2/2006 | Varadharajulu | |
| 7,028,356 B2 | 4/2006 | Somasundaram | |
| 7,125,167 B2 | 10/2006 | Alakkat | |
| 9,055,873 B2 * | 6/2015 | Boda | A61B 6/0457 |
| 9,282,937 B2 * | 3/2016 | Shibata | A61B 6/0407 |
| 9,833,208 B2 * | 12/2017 | Annano | A61B 6/037 |
| 2004/0172145 A1 | 9/2004 | Varadharajulu | |
| 2005/0058257 A1 * | 3/2005 | Fischer | A61B 6/04 378/196 |
| 2016/0015345 A1 * | 1/2016 | Noda | A61B 6/4441 378/196 |
| 2016/0038115 A1 * | 2/2016 | Kosugi | A61B 6/0457 378/209 |

(Continued)

FOREIGN PATENT DOCUMENTS

| | | |
|---|---|---|
| EP | 2792304 A4 * | 8/2015 |
| JP | 2004-121604 A | 4/2004 |
| JP | 2004-159815 A | 6/2004 |

*Primary Examiner* — Kiho Kim
(74) *Attorney, Agent, or Firm* — Muir Patent Law, PLLC (57) ABSTRACT

An X-ray fluoroscopic imaging apparatus is capable of easily setting a region of interest and maintaining a source object distance, such as in cases where a mechanism for moving a top board upward and downward is not provided or even in cases where it is desired to perform control without moving the top board upward and downward. In some examples, a C-arm supports an X-ray tube and a flat panel detector to face each other. An examination table equipped with a movable top board is movable in a longitudinal direction and inclinable. The movable top board may be moved in the longitudinal direction in a state in a which an inclination angle is maintained until a position in a perpendicular direction with respect to the movable top board after inclination changed matches a position in the perpendicular direction with respect to the movable top board before the inclination with respect to a height in the vertical direction and move a C-arm by a distance moved in parallel to a horizontal plane.

3 Claims, 8 Drawing Sheets

(56) References Cited

U.S. PATENT DOCUMENTS

| | | | |
|---|---|---|---|
| 2016/0045177 A1* | 2/2016 | Barth | A61B 6/4452 378/198 |
| 2016/0278720 A1* | 9/2016 | Tanaka | A61B 6/0457 |
| 2018/0214103 A1* | 8/2018 | Okubo | A61B 6/463 |

* cited by examiner

X-RAY FLUOROSCOPIC IMAGING APPARATUS

TECHNICAL FIELD

The present invention relates to an X-ray fluoroscopic imaging apparatus for performing fluoroscopy or imaging, and more particularly to a technique for inclining (hereinafter referred to as "tilting motion") a movable top board in cases where an examination table having a movable top board movable in a longitudinal direction and inclinable with respect to a main body is provided.

BACKGROUND ART

Conventionally, in this type of apparatus, the top board is made to perform a tilting motion by rotating the top board about the axis of the lateral direction of the top board (see, for example, Patent Documents 1 to 7). Note that Patent Document 2: Japanese Unexamined Patent Application Publication No. 2004-159815 is a Japanese patent family of Patent Document 7: U.S. Pat. No. 7,000,271. In this type of apparatus, when a subject (patient) laid on the top board is inclined by the tinting motion, the region of interest (ROI: Region of Interest) shifts, the distance (SOD: Source Object Distance) between the X-ray tube and the subject changes, and the X-ray passing angle changes. For this reason, it is required to automatically maintain the region of interest in accordance with the tilting motion as described in each Patent Document.

PRIOR ART DOCUMENT

[Patent Document]
[Patent Document 1] Japanese Unexamined Patent Application Publication No. 2004-121604
[Patent Document 2] Japanese Unexamined Patent Application Publication No. 2004-159815
[Patent Document 3] U.S. Pat. No. 5,930,328
[Patent Document 4] U.S. Pat. No. 6,416,219
[Patent Document 5] U.S. Pat. No. 7,028,356
[Patent Document 6] U.S. Pat. No. 7,125,167
[Patent Document 7] U.S. Pat. No. 7,000,271

SUMMARY OF THE INVENTION

Problems to be Solved by the Invention

However, in the case of the conventional example having the configuration described above, there are following problems.

That is, as described in each Patent Document, it is conceivable to move the top board in the vertical direction (upward and downward). However, in cases where it is not provided with a mechanism for moving the top board upward and downward, or even in cases where it is desired to perform control without moving the top board upward and downward, it is desired to easily set the region of interest and maintain the SOD.

The present invention has been made in view of the aforementioned circumstances, and aims to provide an X-ray fluoroscopic imaging apparatus capable of easily setting a region of interest and maintain an SOD in cases where a mechanism for moving a top board upward and downward is not provided or even in cases where it is desired to perform control without moving the top board upward and downward.

Means for Solving the Problems

In order to attain such an object, the present invention has the following configuration.

That is, an X-ray fluoroscopic imaging apparatus for performing fluoroscopy or imaging includes: a support means configured to support an X-ray tube and an X-ray detector so as to face each other; an examination table provided with a movable top board movable in a longitudinal direction and inclinable with respect to a main body; and a control means configured to perform control of moving the movable top board in the longitudinal direction in a state in which an inclination angle is maintained until a position in a perpendicular direction with respect to the movable top board after inclination changed in accordance with the inclination of the movable top board matches a position in the perpendicular direction with respect to the movable top board before the inclination with respect to a height in the vertical direction, and control of moving the support means by a distance moved in parallel to a horizontal plane due to the inclination and a movement in the longitudinal direction.

[Functions and Effects] According to the X-ray fluoroscopic imaging apparatus of the present invention, in cases where the support means for supporting the X-ray tube and the X-ray detector so as to face each other and the examination table having the movable top board which is movable in the longitudinal direction and inclinable with respect to the main body are provided, the control means performs the following control. That is, when the movable top board is inclined (tilting motion), the position in the perpendicular direction with respect to the movable top board before inclination is changed by the tilting motion. Under the circumstance, a control is performed so as to move the movable top board in the longitudinal direction in a state in which the inclination angle is maintained until the position in the perpendicular direction with respect to the movable top board after inclination changed in accordance with the inclination coincides with the position in the perpendicular direction with respect to the movable top board after inclination with respect to the height in the vertical direction. With this control, the height of the region of interest coincides but the position in the horizontal direction shifts. For this reason, a control is performed so as to translate the support means by the distance moved in parallel to a horizontal plane due to the inclination and the movement in the longitudinal direction. By these two controls (the control on the longitudinal directional movement of the movable top board and the control on the translational movement of the support means), the region of interest is set. As a result, in cases where a mechanism for moving a top board upward and downward is not provided or even in cases where it is desired to perform control without moving a top board upward and downward. it is possible to easily set the region of interest and maintain the SOD.

In the aforementioned invention, the support means may be configured to be inclinable in according to the inclination angle of the movable top board. Since the support means is inclined in accordance with the inclination angle of the movable top board, performing fluoroscopy or imaging can be performed without causing the change of the X-ray passing angle before and after the inclination. In cases where the region of interest is set so as to coincide with the rotation center on the inclination of the support means, it is enough only to rotate the support means at the inclination angle according to the inclination angle of the movable top board. However, due to the circumstances in constraints on the installation of each component or due to the design, there may be cases where it is not possible to match the region of interest with the rotation center on the inclination of the support means.

In this case, when the support means is inclined in accordance with the inclination angle of the movable top board, the position of the region of interest shifts in the horizontal direction and the vertical direction. Therefore, the control means is configured to perform the control of translating the support means after inclination by the distance moved in parallel to a horizontal plane due to the inclination of the support means and translating the support means after inclination by the height moved in the vertical direction due to the inclination of the support means. By these two controls (control on the horizontal translational movement of the support means and control on the vertical translational movement of the support means), the region of interest matches before and after the inclination.

Note that as for the order of performing these two controls (the control on the horizontal translational movement of the support means and the control on the vertical translational movement of the support means), it is not particularly limited. After the control on the horizontal translational movement of the support means, a control on the vertical translation movement of the support means may be carried out, and after the control on the vertical translational movement of the support means, the control on the horizontal translational movement of the support means may be carried out.

Effects of the Invention

According to the X-ray fluoroscopic imaging apparatus of the present invention, in cases where the support means for supporting the X-ray tube and the X-ray detector so as to face each other and the examination table having the movable top board movable in the longitudinal direction and inclinable with respect to the main body are provided, the control means performs the following control. That is, a control means performs control of moving the movable top board in the longitudinal direction in a state in which an inclination angle is maintained until a position in a perpendicular direction with respect to the movable top board after an inclination changed in accordance with the inclination of the movable top board matches a position in the perpendicular direction with respect to the movable top board before the inclination with respect to a height in the vertical direction and moving the support means by a distance moved in parallel to a horizontal plane due to the inclination and a movement in the longitudinal direction. As a result, it is possible to easily set the region of interest and maintain the SOD in cases where a mechanism for moving a top board upward and downward is not provided or even in cases where it is desired to perform control without moving a top board upward and downward.

BRIEF DESCRIPTION OF THE DRAWINGS

In FIG. 6, (a) to (d) illustrate schematic diagrams on the movements of the movable top board and the C-arm according to Example 1.

EMBODIMENTS FOR CARRYING OUT THE INVENTION

Example 1

Hereinafter, Example 1 of the present invention will be described with reference to the drawings.

Figure 1:
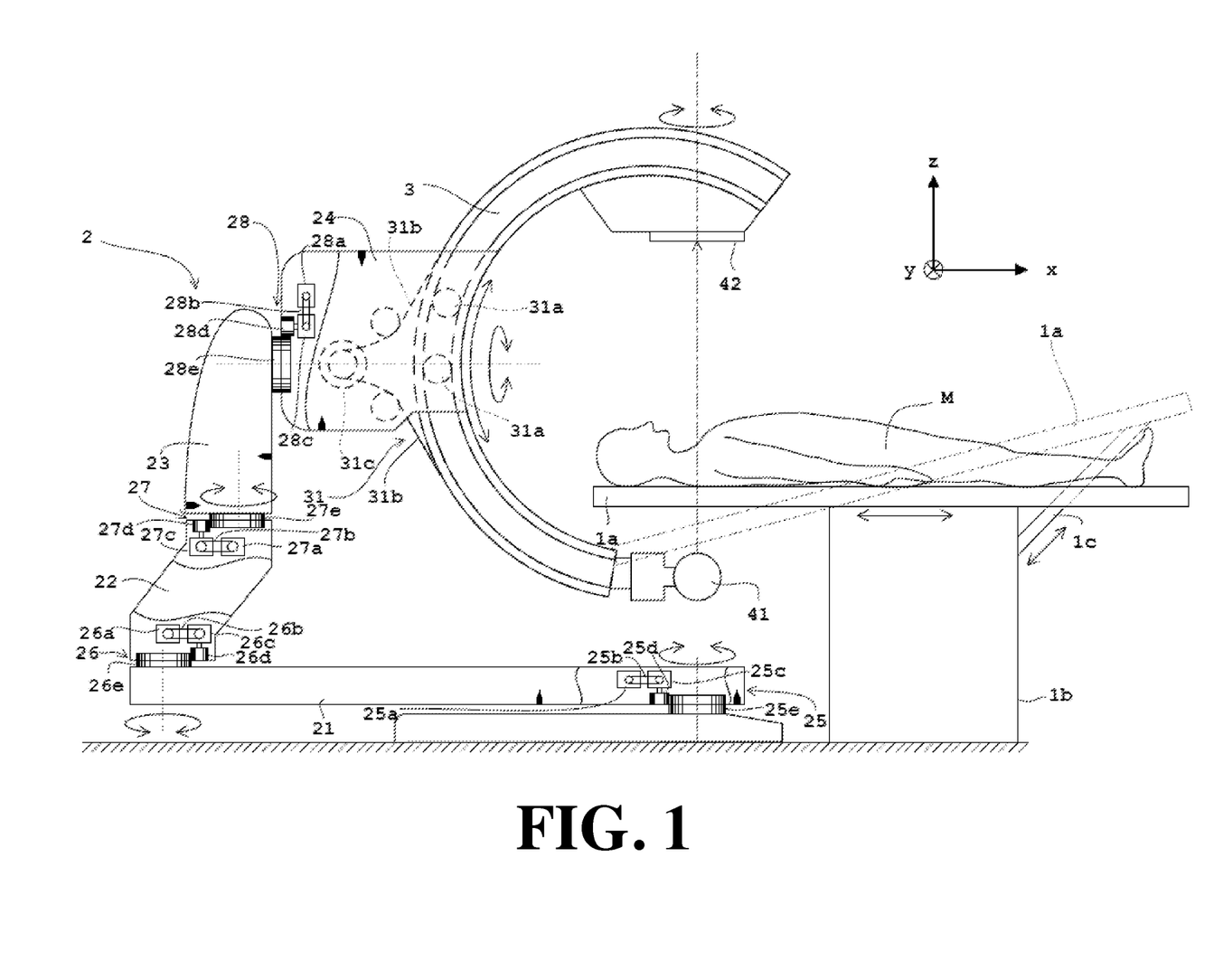
FIG. 1 is a side view of an X-ray fluoroscopic imaging apparatus provided with a C-arm according to each Example.
Figure 2:
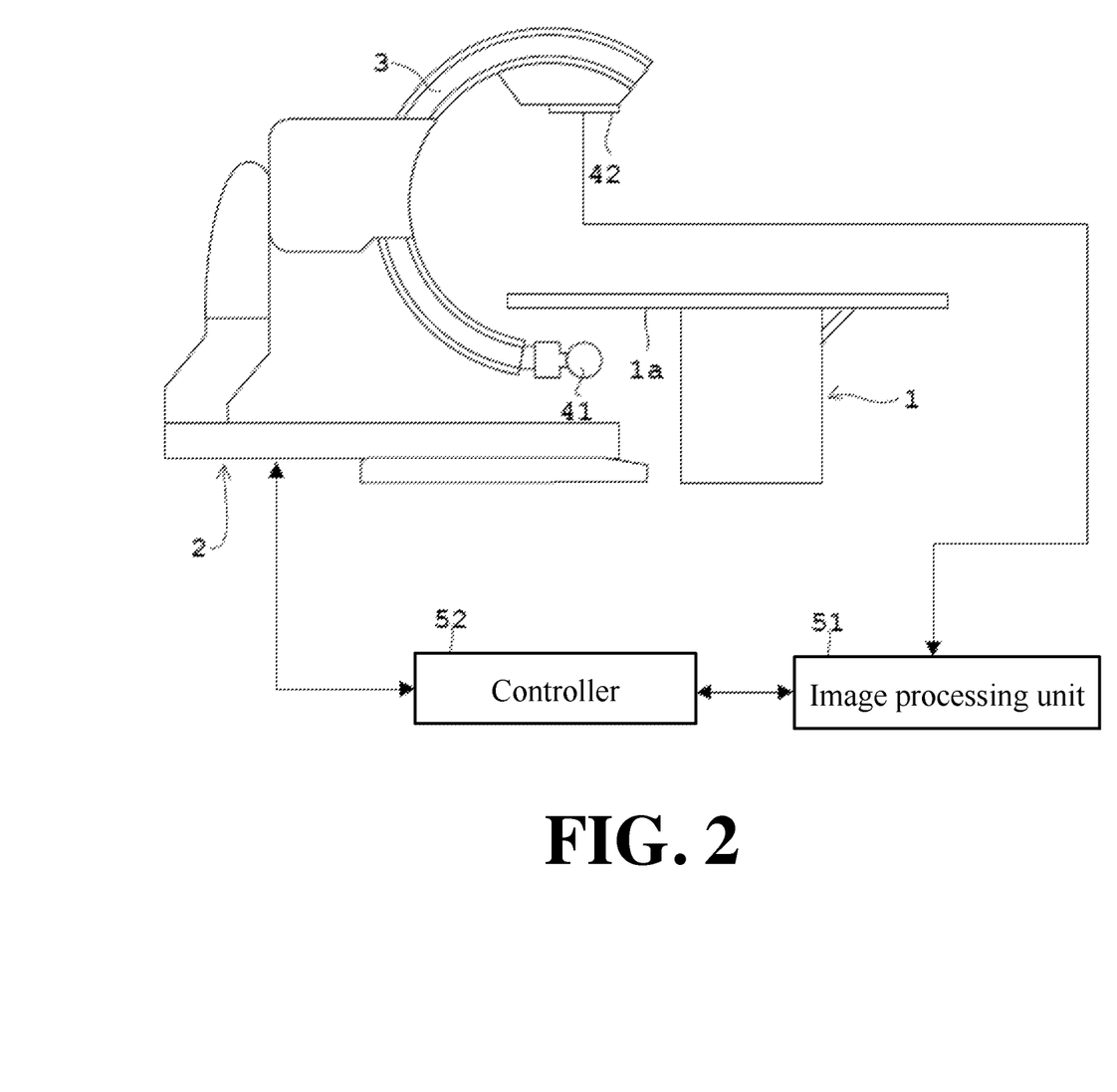
FIG. 2 is a block diagram of an X-ray fluoroscopic imaging apparatus according to each Example.

FIG. 1 is a side view of an X-ray fluoroscopic imaging apparatus provided with a C-arm according to each Example, and FIG. 2 is a block diagram of an X-ray fluoroscopic imaging apparatus according to each Example.

As shown in FIG. 1, the X-ray fluoroscopic imaging apparatus according to this Example 1 is provided with an examination table 1 having a movable top board 1a which is configured to place a subject M thereon and movable in the longitudinal direction and inclinable with respect to a main body 1b, a base 2, and a C-arm 3. The apparatus is further provided with an image processing unit 51 and a controller 52 as shown in FIG. 2. Note that the above description will also be applied to Example 2 which will be described later. The main body 1b of the examination table 1 is provided with a jack 1c which supports the bottom surface of the movable top board 1a. The jack 1c is configured to extend and contract in the direction of the arrow shown in the figure. The jack 1c is configured to extend and contract to rotate the movable top board 1a about the axis of the movable top board 1a in the lateral direction (y-axis in the figure) to thereby perform the tilting motion of the movable top board 1a. The type of the jack 1c is not particularly limited as exemplified by a mechanical type, a liquid operation type, a pneumatic type, and the like. Note that the jack may be configured to make the movable top board perform the tilting motion by expanding/contracting in the vertical direction without expanding/contracting in the oblique direction. The C-arm 3 corresponds to the support means in the present invention, and the controller 52 corresponds to the control means in the present invention.

The base 2 is provided with a first base unit 21 installed on the floor surface (x-y plane in the figure), a second base unit 22 supported by the first base unit 21, a third base unit 23 supported by the second base unit 22, and a C-arm support unit 24 supported by the third base unit 23. The C-arm 3 is supported by the C-arm support unit 24. The one end of the C-arm 3 supports the X-ray tube 41 and the other end of the C-arm 3 supports a flat panel type X-ray detector (FPD: Flat Panel Detector) 42. In this way, the C-arm 3 supports the X-ray tube 41 and the flat panel X-ray detector (FPD) 42 so as to face each other.

Also provided is a first base moving unit 25 for rotationally moving the first base unit 21 with respect to the floor surface about the vertical axis (Z-axis in the figure). The first base moving unit 25 is provided with a motor 25a, a belt 25b for transmitting the rotation of the motor 25a, a gear box 25c for converting the rotation transmitted to the belt 25b into the rotation about the vertical axis, a gear 25d for transmitting the rotation about the vertical axis from the gear box 25c, and a gear 25e engaged with the gear 25d. The gear 25e is fixed to the floor surface with a bearing (not shown) interposed therebetween. As the motor 25a rotates, the gear 25e rotates about the vertical axis via the belt 25b, the gear box 25c, and the gear 25d, and the first base unit 21 rotates about the vertical axis with respect to the floor surface in accordance with the rotation of the gear 25e.

As the first base unit 21 is rotationally moved about the vertical axis by the first base moving unit 25, the second base unit 22 supported by the first base unit 21 is also rotationally moved about the vertical axis, the third base unit 23 supported by the second base unit 22 is also rotationally moved about the vertical axis, the C-arm support unit 24 supported by the third base unit 23 is also rotationally moved about the vertical axis, the C-arm 3 supported by the C-arm support unit 24 is also rotationally moved about the vertical axis, and the X-ray tube 41 and the FPD 42 supported by the C-arm 3 are also rotationally moved about the vertical axis. As described above, the first base moving unit 25 rotationally moves the X-ray tube 41 and the FPD 42 about the vertical axis.

Further provided is a second base moving unit 26 for rotationally moving the second base unit 22 about the vertical axis with respect to the first base unit 21. The second base moving unit 26 is provided with a motor 26a, a belt 26b for transmitting the rotation of the motor 26a, a gear box 26c for converting the rotation transmitted to the belt 26b into the rotation about the vertical axis, a gear 26d for transmitting the rotation around the vertical axis from the gear box 26c, and a gear 26e engaged with this gear 26d. The gear 26e is fixed to the first base unit 21 in a state in which a bearing (not shown) is interposed therebetween. As the motor 26a is rotationally driven, the gear 26e is rotated about the vertical axis via the belt 26b, the gear box 26c, and the gear 26d. In accordance with this rotation of the gear 26e, the second base unit 22 is rotationally moved about the vertical axis with respect to the first base unit 21.

As the second base unit 22 is rotationally moved about the vertical axis by the second base moving unit 26, the third base unit 23 supported by the second base unit 22 is also rotationally moved about the vertical axis, the third base unit 23 supported by the second base unit 22 is also rotationally moved about the vertical axis, the C-arm support unit 24 supported by the third base unit 23 is also rotationally moved about the vertical axis, the C-arm 3 supported by the C-arm support unit 24 is also rotationally moved about the vertical axis, and the X-ray tube 41 and the FPD 42 supported by the C-arm 3 are also rotationally moved about the vertical axis. As described above, the second base moving unit 26 makes the X-ray tube 41 and the FPD 42 rotationally move about the vertical axis.

Further provided is a third base moving unit 27 for rotationally moving the third base unit 23 about the vertical axis with respect to the second base unit 22. The third base moving unit 27 is provided with a motor 27a, a belt 27b for transmitting the rotation of the motor 27a, a gear box 27c for converting the rotation transmitted to the belt 27b into the rotation about the vertical axis, a gear 27d for transmitting the rotation about the vertical axis from the gear box 27c, and a gear 27e engaged with this gear 27d. The gear 27e is fixed to the second base unit 22 in a state in which a bearing (not shown) is interposed therebetween. As the motor 27a is rotationally driven, the gear 27e is rotated about the vertical axis via the belt 27b, the gear box 27c, and the gear 27d. In accordance with this rotation of the gear 27e, the third base unit 23 is rotationally moved about the vertical axis with respect to the second base unit 22.

As the third base unit 23 is rotationally moved about the vertical axis by the third base moving unit 27, the C-arm support unit 24 supported by the third base unit 23 is also rotationally moved about the vertical axis, the C-arm 3 supported by the C-arm support unit 24 is also rotationally moved about the vertical axis, and the X-ray tube 41 and the FPD 42 supported by the C-arm 3 are also rotationally moved about the vertical axis. As described above, the third base moving unit 27 makes the X-ray tube 41 and the FPD 42 rotationally move about the vertical axis.

In this way, since the first base moving unit 25, the second base moving unit 26, and the third base moving unit 27 are provided, there exist rotation axes composed of three different vertical axes. By rotationally moving each of them about the respective vertical axes, the C-arm 3 is translated together with the X-ray tube 41 and the FPD 42 on the horizontal plane (the x-y plane in the figure).

Further provided is a C-arm support moving unit 28 configured to rotationally move the C-arm support unit 24 with respect to the third base unit 23 about an axis (x-axis in the figure) parallel to the longitudinal direction of the movable top board 1a when the movable top board 1a is not inclined and parallel to the floor surface. The C-arm support moving unit 28 is provided with a motor 28a, a belt 28b for transmitting the rotation of the motor 28a, a gear box 28c for converting the rotation transmitted to the belt 28b into the rotation about the x-axis, a gear 28d for transmitting the rotation about the x-axis center from the gear box 28c, and the gear 28e engaged with the gear 28d. The gear 28e is fixed to the third base unit 23 in a state in which a bearing (not shown) is interposed therebetween. As the motor 28a is rotationally driven, the gear 28e is rotated about the x-axis via the belt 28b, the gear box 28c, and the gear 28d. In accordance with this rotation of the gear 28e, the C-arm support unit 24 is rotationally driven about the x-axis with respect to the third base unit 23.

As the C-arm support unit 24 is rotationally moved about the x-axis by the C-arm support moving unit 28, the C-arm 3 supported by the C-arm support unit 24 is also rotationally moved about the x-axis, and the X-ray tube 41 and the FPD 42 supported by the C-arm 3 are also rotationally moved about the x-axis. As described above, the C-arm support moving unit 28 makes the X-ray tube 41 and the FPD 42 rotationally move about the x-axis.

Also provided is a C-arm support moving unit 31 for rotating the C-arm 3 about the axis (y-axis in the figure) parallel to the lateral direction of the movable top board 1a. The C-arm 3 is formed in a rail shape. The C-arm support moving unit 31 is provided with two bearings 31a fitted in the groove of the C-arm 3, a belt 31b arranged along the outer circumferential surface of the C-arm 3, and a motor 31c for winding a part of the belt 31b. As the motor 31c is rotationally driven, the belt 31b circulates. In accordance with the circular movement, the C-arm 3 slides with respect to the bearing 31a. In accordance with this sliding movement, the C-arm 3 rotates about the y-axis. The X-ray tube 41 and the FPD 42 supported by the C-arm 3 are also rotated about the y-axis. As described above, the C-arm support moving unit 31 makes the X-ray tube 41 and the FPD 42 rotationally move about the y-axis.

As described above, the C-arm 3 that supports the X-ray tube 41 and supports the FPD 42 is formed in a curved shape of "C" along the direction of the rotational movement about the y-axis by the C-arm support moving unit 31. Therefore, it can be said that the X-ray tube 41 and the FPD 42 rotationally moves about the y-axis along the curved direction of the C-arm 3. Further, the C-arm support moving unit 28 rotationally moves the C-arm 3 in the direction of the rotational movement about the x-axis which is a direction different from the rotational movement about the y-axis of the C-arm 3. Therefore, it can be said that the X-ray tube 41 and the FPD 42 are rotationally moved about the x-axis.

It may be configured to provide a C-arm parallel moving unit (not shown) for horizontally translating the X-ray tube 41 and the FPD 42 by translating the first base unit 21, the second base unit 22, the third base unit 23, the C-arm support unit 24, or the C-arm 3 in the horizontal direction (for example, the x-direction or the y-direction shown in the figure), or provide an FPD moving unit (not shown) for rotationally moving the C-arm 3 and the FPD 42 about a support axis supporting them. Further, for the purpose of adjusting the C-arm 3 itself or the deflection (positional deviation) due to the own weight of the X-ray tube 41 and the FPD 42 supported by the C-arm 3, an adjustment unit (not shown) for rotationally moving the C-arm in the deflection direction may be provided. It may also be provided with a C-arm vertically moving unit (not shown) for translating the X-ray tube 41 and the FPD 42 along the vertical axis by vertically moving the C-arm support unit 24 or the C-arm 3 along the vertical axis.

It may also be provided with an FPD moving unit (not shown) for translating the FPD 42 along the support axis direction supporting the FPD 42. In this case, since the support axis that supports the FPD 42 by the C-arm 3 is parallel to the direction of the perpendicular line (i.e., the irradiation center axis) drawn from the X-ray tube 41 to the FPD 42, the FPD 42 is translated along the perpendicular line by translating the FPD moving unit by the FPD moving unit along the support axis direction. That is, the FPD moving unit makes the distance (that is, the SID (Source Image Distance)) along which the perpendicular line is drawn from the X-ray tube 41 to the FPD 42 variable, so the X-ray tube 41 and the FPD 42 are moved in parallel along the perpendicular direction.

The movable top board 1a, the base 2, and the C-arm 3 are moved as described above, and an X-ray detection signal obtained by the FPD 42 detecting the X-rays irradiated from the X-ray tube 41 is processed by the image processing unit 51 to obtain an X-ray image of the subject M. In the case of performing a fluoroscopic inspection, a plurality of X-ray images is obtained sequentially by irradiating X-rays with less dose than in X-ray imaging, and each X-ray image is displayed on a monitor (not shown) in real time. In the case of performing X-ray imaging, X-rays are irradiated from the X-ray tube 41, and a single X-ray image is outputted to a monitor to be displayed or to a printer (not shown) to be printed out.

The controller 52 (see FIG. 2) collectively controls each configuration of the X-ray fluoroscopic imaging apparatus. In particular, the controller 52 controls the jack 1c, and the moving units 25 to 28, and 31. In this Example 1, a control of moving the movable top board 1a in the longitudinal direction in a state in which the inclination angle is maintained until a position in the perpendicular direction with respect to the movable top board 1a after inclination changed in accordance the inclination matches the position in the perpendicular direction with respect to the movable top board 1a before inclination with respect to the height in the vertical direction and translating the C-arm 3 by the distance moved parallel to the horizontal plane due to the inclination and the movement in the longitudinal direction. The specific control in Example 1 will be described later. Note that in FIG. 2, for the sake of convenience of illustration, the lines connecting the controller 52 to the configurations controlled by the controller 52 are omitted.

The image processing unit 51 and the controller 52 are composed of a central processing unit (CPU) or the like. Note that the image processing unit 51 may be configured by a GPU (Graphics Processing Unit) or the like.

Figure 3:
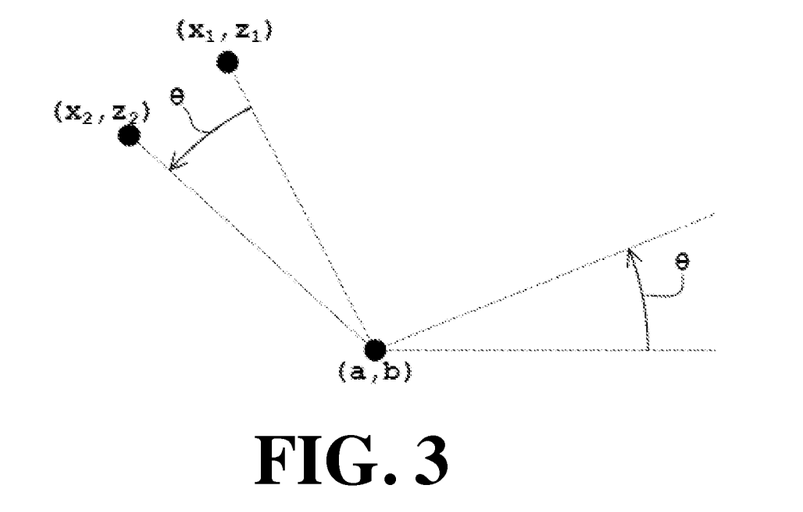
FIG. 3 is a schematic view for explaining the change of the coordinate in accordance with the inclination of the movable top board.
Figure 4:
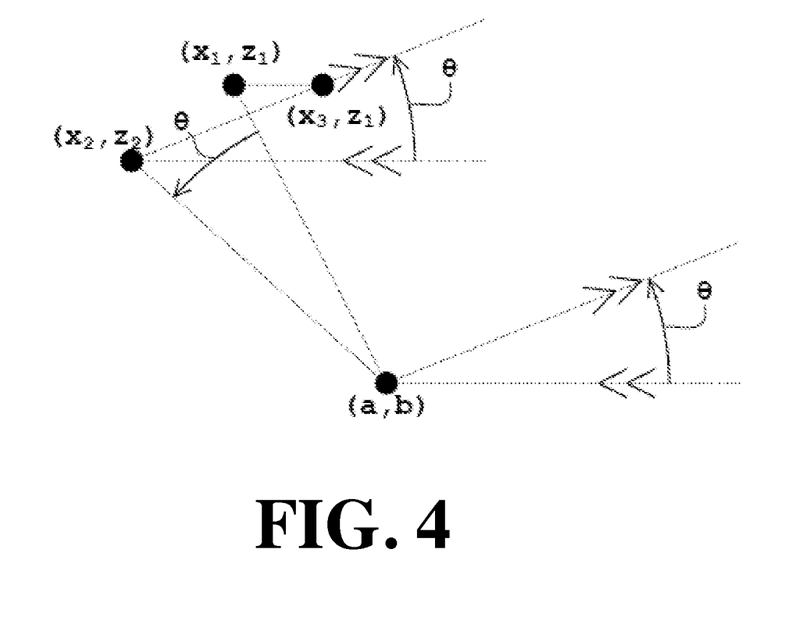
FIG. 4 is a schematic view for explaining the change of the coordinate in accordance with the movement of the movable top board in the longitudinal direction after inclination.
Figure 5:
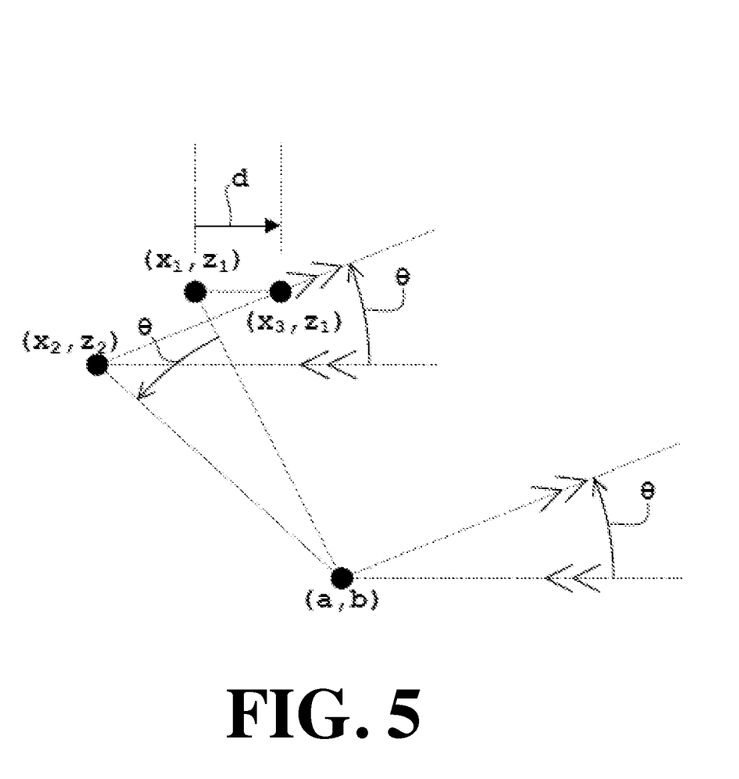
FIG. 5 is a schematic diagram for explaining when the C-arm is moved by the distance moved in parallel to the horizontal plane due to the inclination and the longitudinal movement of the movable top board.

Next, the specific control in Example 1 will be described with reference to FIG. 3 to FIG. 6. FIG. 3 is a schematic view for explaining the coordinate which changes when the movable top board is inclined. FIG. 4 is a schematic view for explaining the coordinate which changes when the movable top board after inclination is moved in the longitudinal direction. FIG. 5 is a schematic view for explaining the translational movement of the C-arm by the distance moved parallel to the horizontal plane due to the inclination and the longitudinal movement of the movable top board after inclination. FIG. 6(a) to FIG. 6(d) are schematic diagrams related to the operations of the movable top board and the C-arm according to Example 1. Note that in FIG. 3 to FIG. 5, the illustrations of the examination table 1, the movable top board 1a, the base 2, the C-arm 3, the X-ray tube 41, and the FPD 42 are omitted.

As shown in FIG. 3, the position $(x_1, z_1)$ of the region of interest will be described as a representative of the position in the perpendicular direction with respect to the movable top board 1a (see FIG. 1 and FIG. 2) before inclination. The coordinate of the rotation center on the inclination is denoted by (a, b), the inclination angle is denoted by θ, and the position changed in accordance with the inclination is denoted by $(x_2, z_2)$. Therefore, the position $(x_1, z_1)$ of the region of interest changes to the position $(x_2, z_2)$ in accordance with the tilting motion. Using the rotation matrix, each position is represented by a relational expression, such as the following (1) and (2), taking the coordinate (a, b) of the rotation center into account.

$$x_2 - a = (x^1 - a)\cos\theta - (z_1 - b)\sin\theta \quad (1)$$

$$z_2 - b = (x_1 - a)\sin\theta + (z_1 - b)\cos\theta \quad (2)$$

As shown in FIG. 4, the line segments parallel to the movable top board 1a before inclination (see FIG. 1 and FIG. 2) are indicated by "<<" (see also FIG. 5), and the line segment parallel to the movable top board 1a after inclination are indicated by ">>" (see also FIG. 5). When the movable top board 1a is moved in the longitudinal direction while maintaining the inclination angle θ, the position $(x_2, z_2)$ changes along the line segment indicated by "<<". The position which is the same in height $z_1$ in the vertical direction among the position $(x_1, z_1)$ of the region of interest and changed from the position $(x_2, z_2)$ along the line segment indicated by "<<" is denoted by $(x_3, z_1)$.

In other words, when the movable top board 1a is moved in the longitudinal direction in a state in which the inclination angle θ is maintained until the position $(x_2, z_2)$ which is changed in accordance with the inclination and represents a position in the perpendicular direction with respect to the movable top board 1a after inclination matches the position $(x_1, z_1)$ of the region of interest which represents the position in the perpendicular direction with respect to the movable top board 1a before inclination, the position $(x_2, z_2)$ becomes the position $(x_3, z_1)$. Therefore, the unknown coordinate $x_3$ is expressed by the following expression (3).

$$(x_3-x_2)\tan\theta = z_1-z_2 \qquad (3)$$

As shown in FIG. 5, in the same manner as in FIG. 4, the line segments parallel to the movable top board 1a before inclination (see FIG. 1 and FIG. 2) are indicated by "<<", and the line segments parallel to the movable top board 1a after inclination are indicated by ">>". When the distance moved in parallel to the horizontal plane due to the inclination and the longitudinal movement of the movable top board 1a after inclination is denoted by "d" (where the distance d>0), the distance "d" is represented by the absolute value of the difference between $x_1$ and $x_3$ as shown in the following expression (4). Then, the C-arm 3 (see FIG. 1 and FIG. 2) is translated by the distance "d" on the horizontal plane together with the X-ray tube 41 (see FIG. 1 and FIG. 2) and the FPD 42 (see FIG. 1 and FIG. 2).

$$D=|x_3-x_1| \qquad (4)$$

In accordance with the above-described expressions (1) to (4), the controller 52 (see FIG. 2) controls the operation as shown in FIG. 6(a) to FIG. 6(d). Note that, in FIG. 6, the region of interest is shown by a black circle, and the position changed in accordance with each movement including inclination is shown by a white circle.

The position of the black circle in FIG. 6(a) to FIG. 6(c) corresponds to the position $(x_1, z_1)$ of the region of interest in FIG. 3 to FIG. 5. First, the movable top board 1a before inclination shown in FIG. 6(a) is inclined as shown in FIG. 6(b). The position of the white circle in FIG. 6(b) corresponds to the position $(x_2, z_2)$ in FIG. 3 to FIG. 5.

Subsequently, the movable top board 1a after inclination shown in FIG. 6(b) is moved in the longitudinal direction in a state in which the inclination angle is maintained as shown in FIG. 6(c). This movement in the longitudinal direction is performed until the position $(x_2, z_2)$ comes to the position $(x_3, z_1)$ which coincides with the vertical directional height of the position $(x_1, z_1)$ of the region of interest. The position of the white circle in FIG. 6(c) corresponds to the position $(x_3, z_1)$ in FIG. 4 and FIG. 5.

Subsequently, the C-arm 3 shown in FIG. 6(c) is moved parallel to the horizontal plane by the distance "d" (see FIG. 5) as shown in FIG. 6(d). In this manner, the region of interest indicated by the black circle in FIG. 6(d) is set so as to be positioned at the position $(x_3, z_1)$ in FIG. 4 and FIG. 5.

According to the X-ray fluoroscopic imaging apparatus of Example 1, in cases where the support means (C-arm 3 in each Example) for supporting the X-ray tube 41 and the X-ray detector (in each Example, the flat panel X-ray detector (FPD) 42) and the examination table 1 having the movable top board 1a which is movable in the longitudinal direction with respect to the main body 1b and inclinable, the control means (controller 52 in each Example) performs the following control. That is, when the movable top board 1a is inclined (tilting motion), the position (e.g., the region of interest) in the perpendicular direction with respect to the movable top board 1a is changed by the tilting motion. Under the circumstance, a control of moving the movable top board 1a in the longitudinal direction (e.g., to the position $(x_3, z_1)$) is performed in a state in which the inclination angle is maintained until the position (e.g., the position $(x_2, z_2)$) which is changed in accordance with the inclination and represents the position in the perpendicular direction with respect to the movable top board 1a after the inclination matches the position (e.g., the position $(x_1, z_1)$ of the region of interest) in the perpendicular direction with respect to the movable top board 1a before inclination with respect to the height (e.g., height $z_1$). With this control, the height $z_1$ of the region of interest matches but the position in the horizontal direction shifts. For this reason, a control of translating the support means (C-arm 3) is performed by the distance (the distance "d" in each Example) moved in parallel to the horizontal plane due to the inclination and the movement in the longitudinal direction. By these two controls (the control on the longitudinal directional movement of the movable top board 1a and the control on the translational movement of the C-arm 3 which is the support means), the region of interest is set (for example at the position $(x_3, z_1)$). As a result, it is possible to easily set the region of interest and maintain the SOD in cases where a mechanism for moving a top board upward and downward is not provided or even in cases where it is desired to control without moving a top board upward and downward.

Example 2

Hereinafter, Example 2 of the present invention will be described with reference to the drawings.

Figure 7:
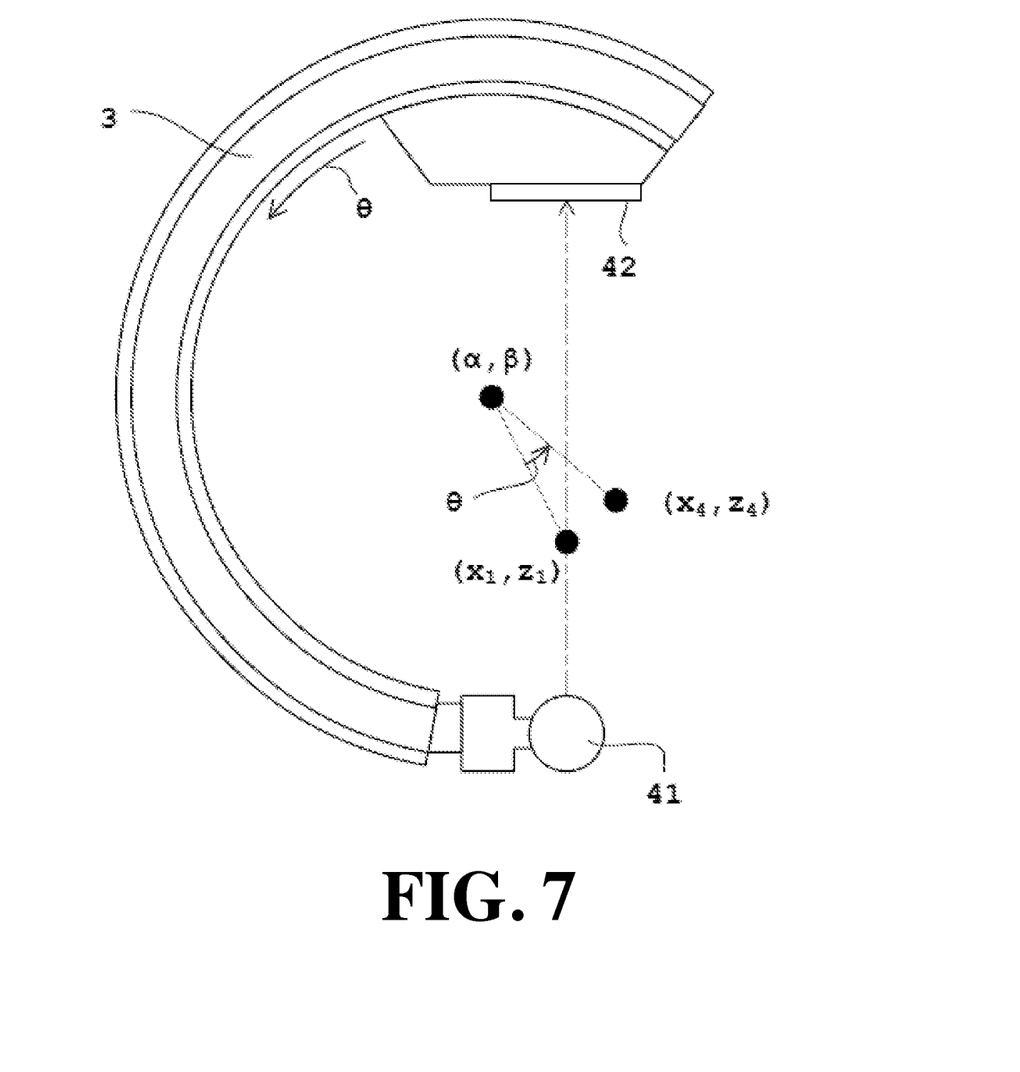
FIG. 7 is a schematic diagram for explaining a coordinate which changes when the C-arm is inclined in cases where the region of interest does not coincide with the rotation center on the C-arm inclination.
Figure 8:
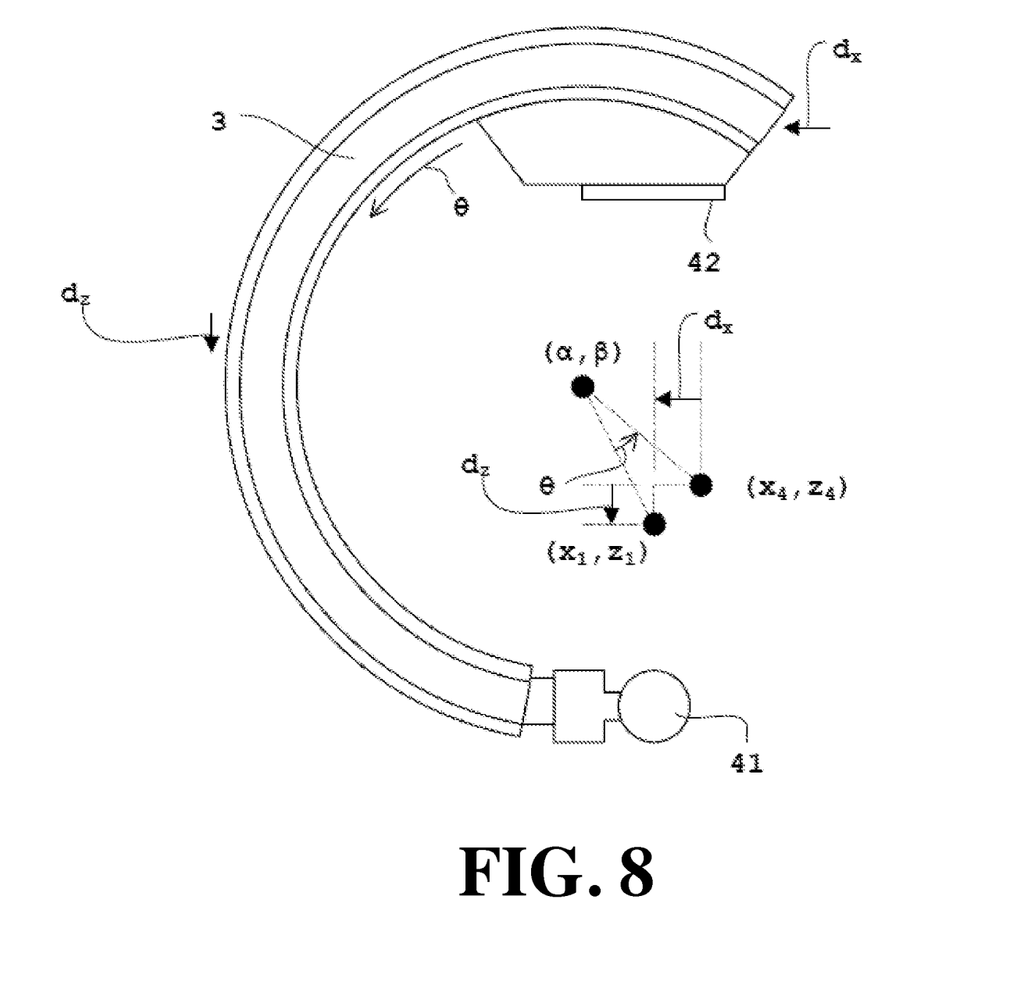
FIG. 8 is a schematic diagram for explaining the translational movement of the C-arm after inclination by the distance/height moved in the horizontal plane/vertical direction due to the inclination of the C-arm in the case of FIG. 7.

FIG. 7 is a schematic diagram for explaining the coordinate which changes when the C-arm is inclined in cases where the region of interest does not coincide with the rotation center on the C-arm inclination. FIG. 8 is a schematic diagram for explaining the translational movement of the C-arm after inclination by the distance/height moved in the horizontal plane/vertical direction due to the inclination of the C-arm in the case of FIG. 7. Note that in Example 2, the X-ray fluoroscopic imaging apparatus shown in FIG. 1 which is the same as the above-described Example 1 is used, which will also be applied to the block diagram of FIG. 2.

Figure 6:
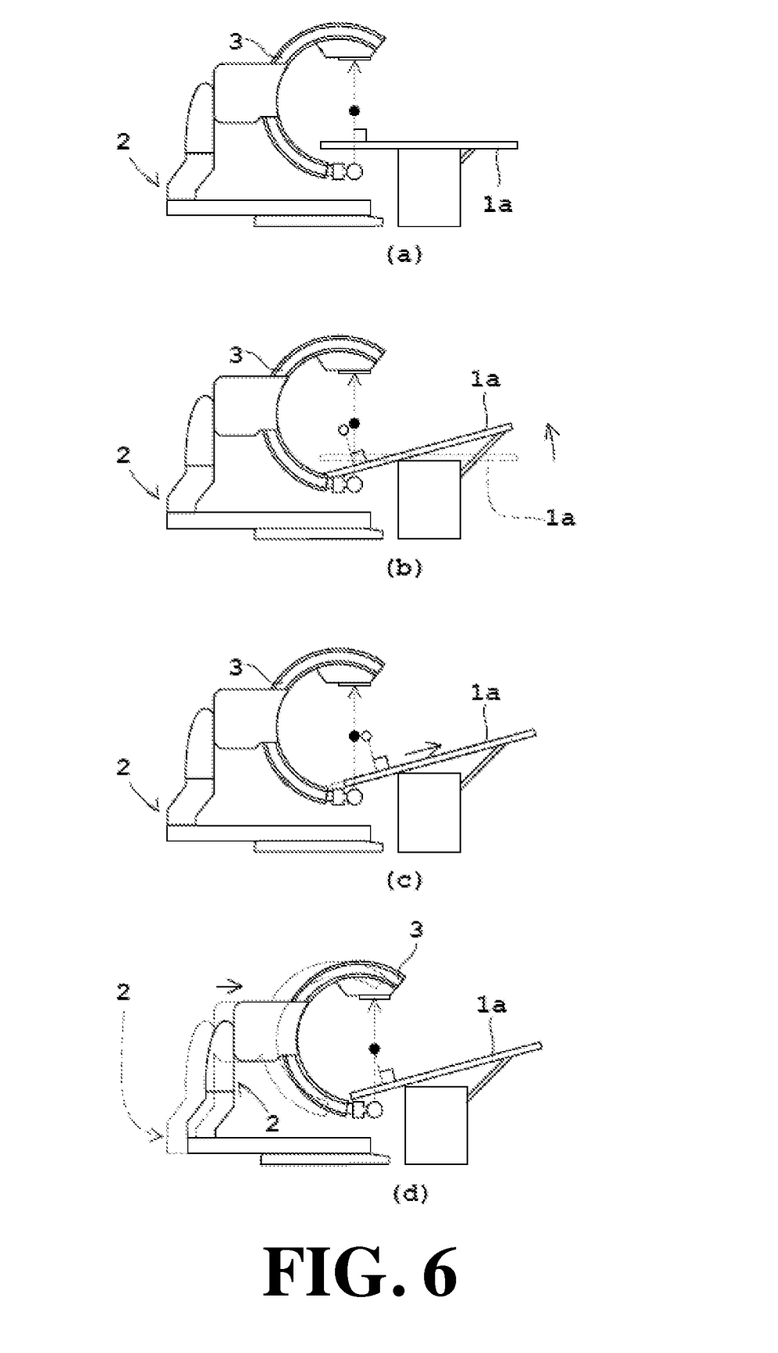

In the above-described Example 1, the C-arm 3 is not inclined. However, as in this Example 2, the C-arm 3 may be inclined in accordance with the inclination angle θ of the movable top board 1a. In cases where the region of interest is set so as to coincide with the rotation (corresponding to the rotation about the y-axis in FIG. 1) center of the C-arm 3, it is enough to translate the C-arm 3 in the same manner as shown in FIG. 6 of Example 1 except that the C-arm 3 is rotated at the inclination angle θ so as to be inclined in accordance with the inclination angle θ of the movable top board 1a. Note that the timing of inclination of the C-arm 3 is not particularly limited as long as the C-arm 3, the X-ray tube 41, and the FPD 42 do not collide with the examination table 1. For example, the C-arm 3 may be inclined at the time point before inclining the movable top board 1a as shown in FIG. 6(a), the C-arm 3 may be inclined at any time point shown in FIG. 6(a) to FIG. 6(d), or the C-arm 3 may be inclined at the time point after the translational movement of the C-arm 3 shown in FIG. 6(d).

In this way, when the region of interest is set so as to coincide with the rotation center on the inclination of the support means represented by the C-arm 3, it is enough to rotate the support means represented by the C-arm 3 at the inclination angle θ so as to be inclined in accordance with the inclination angle θ of the movable top board 1a. However, as shown in FIG. 1, in the case of the design in which the irradiation center axis and the rotation axis on the inclination of the C-arm 3 do not intersect, the region of interest cannot be matched to the rotation center on the inclination of the C-arm 3. As described above, due to the circumstances of the design, there may be cases where it is not possible to match the region of interest to the rotation center on the inclination of the support means represented by the C-arm 3.

Other than the above, even if the irradiation center axis and the rotation axis on the inclination of the C-arm 3 do not intersect, due to the circumstances in the installation constraint of each configuration (for example, the movement restriction to avoid the collision between the C-arm 3, the X-ray tube 41, or the FPD 42 and the examination table 1), there are some cases where the region of interest cannot coincide with the rotation center on the inclination of the support means represented by the C-arm 3.

In these cases, when the support means represented by the C-arm 3 is inclined in accordance with the inclination angle θ of the movable top board 1a, the position of the region of interest shifts in the horizontal direction and the vertical direction. Therefore, in these cases, the controller 52 (see FIG. 2) controls the operation as shown in FIG. 8. In FIG. 7 and FIG. 8, only the C-arm 3, the X-ray tube 41, and the FPD 42 are illustrated, and the illustrations of other configurations (the examination table 1, the movable top board 1a, and the base 2) are omitted. Further, only the C-arm 3, the X-ray tube 41, and the FPD 42 before inclination are shown, and the illustrations of the C-arm 3, the X-ray tube 41, and the FPD 42 after inclination are omitted.

As shown in FIG. 7, the description will be made with reference to the position $(x_1, z_1)$ of the region of interest similarly to FIG. 3 to FIG. 5. Defining that the coordinate of the rotation center on the inclination of the C-arm 3 is $(\alpha, \beta)$, the position changed due to the inclination is defined as $(x_4, z_4)$. Therefore, the position $(x_1, z_1)$ of the region of interest changes to the position $(x_4, z_4)$ due to the inclination. Using the rotation matrix, each position is represented by relational expressions, such as the following relational expressions (5) and (6), taking the coordinate $(\alpha, \beta)$ of the rotation center into account.

$$x_4 - \alpha = (x_1 - \alpha)\cos\theta - (z_1 - \beta)\sin\theta \quad (5)$$

$$z_4 - \beta = (x_1 - \alpha)\sin\theta + (z_1 - \beta)\cos\theta \quad (6)$$

When the region of interest coincides with the rotation center on the inclination of the C-arm 3, since $x_1 = \alpha$ and $z_1 = \beta$, by assigning to the above expressions (5) and (6), $x_4 = \alpha$ and $z_4 = \beta$, and even if the C-arm 3 is inclined, it is obvious that the position of the region of interest does not change from the rotation center.

In this manner, when the C-arm 3 is inclined in accordance with the inclination angle θ of the movable top board 1a (see FIG. 1 and FIG. 2), the position $(x_1, z_1)$ of the region of interest shifts to the position $(x_4, z_4)$ in the horizontal direction and the vertical direction.

As shown in FIG. 8, the distance moved in parallel to the horizontal plane due to the inclination of the C-arm 3 is $d_x$ (distance $d_x > 0$) and the height moved in the vertical direction due to the inclination of the C-arm 3 is $d_z$ ($d_z > 0$), the distance $d_x$ is represented by the absolute value of the difference between $x_1$ and $x_4$ as in the following expression (7), the height $d_z$ is expressed by the absolute value of the difference between $z_1$ and $z_4$ as shown in the following expression (8). Then, the C-arm 3 is translated together with the X-ray tube 41 and the FPD 42 by the distance $d_x$ and is translated by the height $d_z$.

$$d_x = |x_4 - x_1| \quad (7)$$

$$d_z = |z_4 - z_1| \quad (8)$$

In accordance with the abode-described expressions (7) and (8), the controller 52 (see FIG. 2) is configured to perform control. That is, the controller 52 is configured to perform control of translating the C-arm 3 after inclination by the distance $d_x$ moved in parallel to the horizontal plane due to the inclination of the C-arm 3, and control of translating the C-arm 3 after inclination by the height $d_z$ moved in the vertical direction due to the inclination of the C-arm 3. By these two controls (the control on the horizontal translational movement of the support means represented by the C-arm 3 and the control on the vertical translational movement of the support means represented the by C-arm), the region of interest matches before and after inclination. That is, as shown in FIG. 7, even if the position $(x_1, z_1)$ of the region of interest shifts to the position $(x_4, z_4)$ in the horizontal direction and the vertical direction due to the inclination of the C-arm 3, as shown in FIG. 8, by translating the C-arm 3 after inclination from the position $(x_4, z_4)$ by the distance $d_x$/height $d_z$, respectively, the region of interest on the C-arm 3 after inclination is positioned at the position $(x_1, z_1)$ of the region of interest on the C-arm 3 before inclination and coincides therewith.

As for the order of performing these two controls (the control on the horizontal translational movement of the support means represented by the C-arm 3 and the control on the vertical translational movement of the support means represented by the C-arm 3), it is not particularly limited. After controlling of the horizontal translational movement of the support means represented by the C-arm 3, the control on the vertical translational movement of the support means represented by the C-arm 3 may be performed. After controlling of the vertical translational movement of the support means represented by the C-arm 3, the control on the horizontal translational movement of the support means represented by the C-arm 3 may be performed.

Even in cases where the region of interest cannot be matched the rotation center on the inclination of the C-arm 3, as for the timing for inclination the C-arm 3 and the timing for translating the C-arm 3 after inclination by the distance $d_x$/height $d_z$, as long as the C-arm 3, the X-ray tube 41, and the FPD 42 do not collide with the examination table 1, it is not particularly limited. For example, the C-arm 3 may be inclined at the time point before the inclination of the movable top board 1a shown in FIG. 6(a) to translate the C-arm 3 after inclination by the distance $d_x$/height $d_z$. The C-arm 3 may be inclined at any time point shown in FIG. 6(a) to FIG. 6(d) to translate the C-arm 3 after inclination by the distance $d_x$/height $d_z$, respectively. The C-arm 3 may be inclined at a time point after the translational movement of the C-arm 3 shown in FIG. 6(d) to translate the C-arm 3 after inclination by the distance $d_x$/height $d_z$, respectively.

According to the X-ray fluoroscopic imaging apparatus of this Example 2, in the same manner as in the above-described Example 1, in the case in which the support means (C-arm 3 in each Example) for supporting the X-ray tube 41 and the X-ray detector (in each Example, the flat panel X-ray detector (FPD) 42) and the examination table 1 having the movable top board 1a which is movable in the longitudinal direction with respect to the body 1b and is inclinable, the control means (controller 52 in each Example) performs the following control. That is, the control for moving the movable top board 1a in the longitudinal direction (e.g., to the position $(x_3, z_1)$) in a state in which the inclination angle θ is maintained until the position (e.g., $(x_1, z_1)$) of the region of interest) with respect to the movable top board 1a after inclination in the perpendicular direction changed in accordance the inclination matches the positon (e.g., the position ($x_1$, $z_1$) of the region of interest) with respect to the movable top board 1a before inclination with respect to the height (e.g., height $z_1$) in the vertical direction, and translating the support means (C-arm 3) by the distance (the distance "d" in each Example) moved parallel to the horizontal plane due to the inclination and the movement in the longitudinal direction. As a result, it is possible to easily set the region of interest and maintain the SOD in cases where a mechanism for moving a top board upward and downward is not provided or even in cases where it is desired to perform control without moving a top board upward and downward.

Furthermore, in the case of Example 2, since the support means (C-arm 3) is inclined in accordance with the inclination angle θ of the movable top board 1a, performing fluoroscopy or imaging can be performed without causing the change of the X-ray passing angle before and after the inclination.

The present invention is not limited to the aforementioned embodiments, and can be modified as follows.

(1) In each Example described above, although the flat panel type X-ray detector (FPD) is taken as an example of an X-ray detector, as long as it is an X-ray detector which is normally used like an image intensifier (I.I), the X-ray detector is not specifically limited.

(2) In each Example described above, as the support means for supporting the X-ray tube and the X-ray detector so as to face each other, the C-arm 3 shown in FIG. 1, FIG. 2, etc., is taken as an example, but it is not limited to the C-arm 3. For example, the support means may be an arm formed so as to be bent into a U-shape. Further, the support means is not limited to a structure installed on a floor surface, the support means may be a support means suspended from a ceiling.

Figure 9:
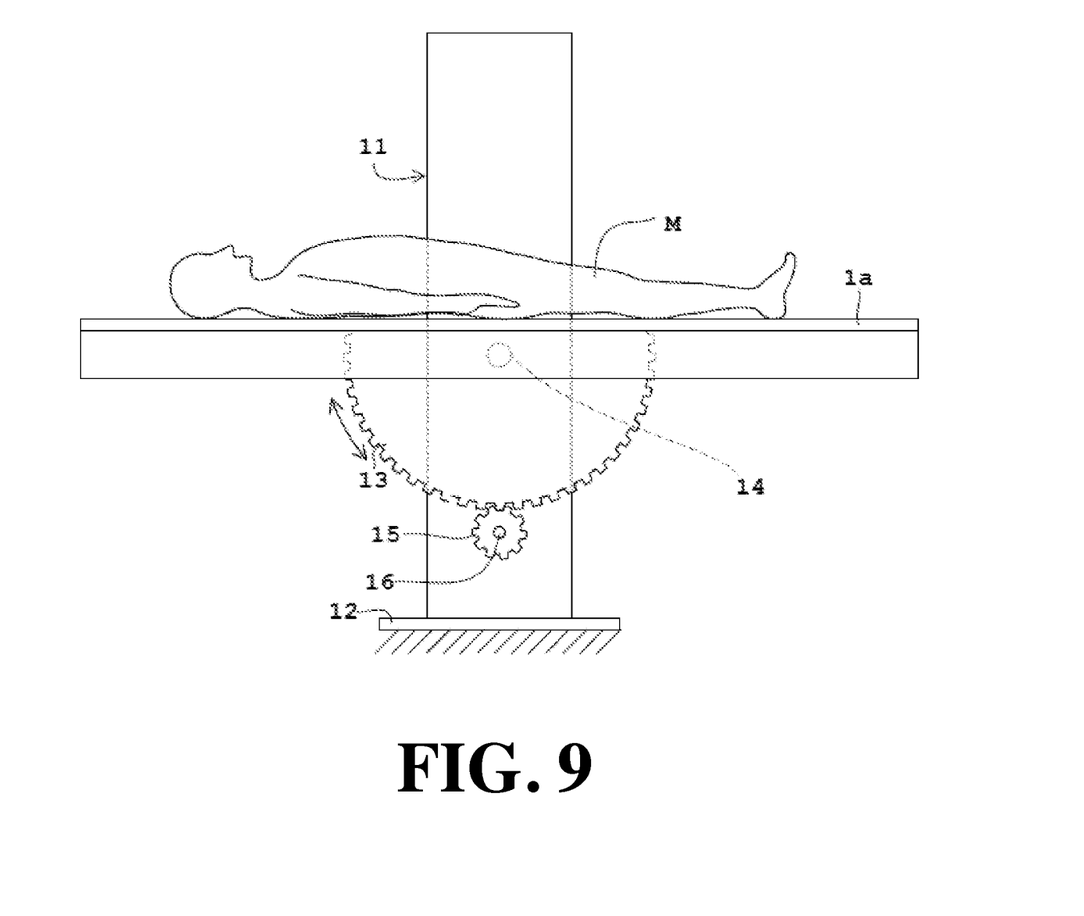
FIG. 9 is a side view of an examination table according to a modified Example.

(3) The examination table having the movable top board movable in the longitudinal direction with respect to the main body is configured to incline the movable top board 1a by the expansion and contraction of the jack 1c as shown in FIG. 1. However, the configuration of the examination table is not specifically limited as long as it is configured to incline the movable top board. There is no particular limitation as long as the movable top board is configured to perform the tilting motion. For example, as shown in FIG. 9, the examination table 1 may also be applied to, in addition to the support columns 11 supporting the movable top board 1a, a configuration having a base 12, a fan-shaped rack 13, a support shaft 14, a pinion 15, a rotation shaft 16, and a motor (not shown). The support column 11 stands on a base 12 installed on a floor surface. The fan-shaped rack 13 inclines the movable top board 1a by rotating the movable top board 1a about the axis of the lateral direction of the movable top board 1a. The support shaft 14 is inserted into the support column 11 and the fan-shaped rack 13. The pinion 15 is engaged with the fan-shaped rack 13. A pinion 15 is disposed at one end of the rotation shaft 16. When a motor rotates the rotation shaft 16, the pinion 15 disposed at one end of the rotation shaft 16 rotates, and in conjunction with the rotation of the pinion 15, the fan-shaped rack 13 engaged with the pinion 15 rotates about the support shaft 14. When the fan-shaped rack 13 is rotated about the support shaft 14 to move the movable top board 1a about the axis of the movable top board 1a in the lateral direction to thereby incline the movable top board 1a. In the case of this configuration, the support shaft 14 becomes the rotation center.

DESCRIPTION OF REFERENCE SYMBOLS 1 examination table
1a movable top board
1b main body (of the examination table)
3 C-arm
41 X-ray tube
42 flat panel type X-ray detector (FPD)
52 controller
θ inclination angle

The invention claimed is:

1. An X-ray fluoroscopic imaging apparatus for performing fluoroscopy or imaging, comprising:
    a support means configured to support an X-ray tube and an X-ray detector so as to face each other;
    an examination table provided with a movable top board movable in a longitudinal direction and inclinable with respect to a main body; and
    a control means configured to perform control of moving the movable top board in the longitudinal direction in a state in which an inclination angle is maintained until a position in a perpendicular direction with respect to the movable top board after the inclination changed in accordance with the inclination of the movable top board matches a position in the perpendicular direction with respect to the movable top board before the inclination with respect to a height in the vertical direction, and control of moving the support means by a distance moved in parallel to a horizontal plane due to the inclination and a movement in the longitudinal direction.

2. The X-ray fluoroscopic imaging apparatus as recited in claim 1,
    wherein the support means is configured to be inclinable in accordance with the inclination angle of the movable top board.

3. The X-ray fluoroscopic imaging apparatus as recited in claim 2,
    wherein the control means further performs control of translating the support means after the inclination by a distance moved parallel to the horizontal plane due to the inclination of the support means and control of translating the support means after the inclination by a distance corresponding to a height moved in the vertical direction due to the inclination of the support means.

* * * * *